United States Patent
Unno et al.

(10) Patent No.: US 7,666,452 B2
(45) Date of Patent: Feb. 23, 2010

(54) BEVERAGE COMPRISING CATHECHINS AND CAFFEINE

(75) Inventors: Tomonori Unno, Shizuoka (JP); Ayumu Nozawa, Shizuoka (JP); Yuko Suzuki, Shizuoka (JP)

(73) Assignee: ITO EN, Ltd., Tokyo (JP)

( * ) Notice: Subject to any disclaimer, the term of this patent is extended or adjusted under 35 U.S.C. 154(b) by 180 days.

(21) Appl. No.: 11/338,746

(22) Filed: Jan. 25, 2006

(65) Prior Publication Data

US 2007/0172530 A1 Jul. 26, 2007

(51) Int. Cl.
*A61K 36/82* (2006.01)

(52) U.S. Cl. ...................................... 424/729

(58) Field of Classification Search ........................ None
See application file for complete search history.

(56) References Cited

U.S. PATENT DOCUMENTS

| | | | |
|---|---|---|---|
| 4,680,193 A | 7/1987 | Lunder et al. | |
| 4,946,701 A | 8/1990 | Tsai et al. | |
| 5,989,557 A | 11/1999 | Bombardelli et al. | |
| 6,096,359 A | 8/2000 | Bombardelli et al. | |
| 6,268,009 B1 | 7/2001 | Ekanayake et al. | |
| 6,821,536 B2 * | 11/2004 | Lines et al. | 426/73 |

FOREIGN PATENT DOCUMENTS

| | | |
|---|---|---|
| EP | 1 527 693 A1 | 5/2005 |
| EP | 1 577 097 A1 | 7/2005 |
| JP | 03-164136 A | 7/1991 |
| JP | 10-004919 A | 1/1998 |
| JP | 2001-197863 A | 7/2001 |
| JP | 2002-187848 A | 7/2002 |
| JP | 2002-370980 A | 12/2002 |
| JP | 2003-171297 A | 6/2003 |
| JP | 2003-212780 A | 7/2003 |
| JP | 2004-035417 A | 2/2004 |
| JP | 2004-129669 A | 4/2004 |
| JP | 2004-180535 A | 7/2004 |
| JP | 2006-087828 A | 3/2006 |
| WO | 97/30597 A1 | 8/1997 |

\* cited by examiner

*Primary Examiner*—Christopher R. Tate
*Assistant Examiner*—Deborah A. Davis
(74) *Attorney, Agent, or Firm*—Sughrue Mion, PLLC

(57) ABSTRACT

A beverage is prepared, which is a beverage containing catechins in ester form (A, mg/L), catechins in free form (B, mg/L), and caffeine (C, mg/L), the contents thereof being $$(A+B)=500 \text{ to } 6000 \text{ mg/L} \quad (1)$$

$$(A)/(A+B)=0.7 \text{ to } 1.0 \quad (2)$$

$$(A)/(C)=6 \text{ to } 27, \quad (3)$$

such that a high concentration of catechins with high biological functionality, improved flavor and improved product quality with low occurrence of sediment is maintained.

13 Claims, No Drawings

BEVERAGE COMPRISING CATHECHINS AND CAFFEINE

BACKGROUND OF THE INVENTION

1. Field of the Invention

The present invention relates to a beverage which contains catechins and has improved taste, such as low bitterness and astringency, and suppressing occurrence of sediment and cream down.

2. Related Art Statement

Catechins contained in tea are reported to have many health effects, such as antioxidant action, blood cholesterol reducing action, hypotensive action, and hyperglycemia inhibitory action. Catechins exist in ester form, such as (−)-epigallocatechin gallate (EGCg), (−)-gallocatechin gallate (GCg), (−)-epicatechin gallate (ECg), and (−)-catechin gallate (Cg), and in free form, such as (−)-epigallocatechin (EGC), (−)-gallocatechin (GC), (−)-epicatechin (EC), (−)-catechin (C), and (+)-catechin ((+) C).

On the other hand, methylxanthines, in particular, caffeine, can be cited as components involved in the taste of tea beverages (in the present invention, beverages containing tea leaf extract are collectively referred to as tea beverages). Caffeine is believed to participate in bitter taste/harsh taste, and a high dose of caffeine provides a beverage with a strongly stimulating taste. Aiming for catechins' health function, if a high dose is ingested, a high concentration of this caffeine derived from tea ends up contained. Caffeine contained in high concentration cannot yield positive feeling from the viewpoint of side effects and bitter taste/harsh taste on the palate.

In recent years, with the expectation of catechins' functionality, attention is concentrated on ingesting catechins more actively, and tea beverages with decreased caffeine have been developed by testing combinations of catechins and caffeine.

Patent Publication No. 3259758 (Japanese Patent Application Laid-Open No. H10-004919) discloses a food and beverage containing caffeine in the amount of 0.1 mass parts or less, and containing cyclodextrin, preferably β-cyclodextrin, in the amount of 0.1 to 20.0 mass parts, preferably 0.1 to 10.0 mass parts, with respect to 1 mass part of catechins.

Patent Publication No. 3162359 (Japanese Patent Application Laid-Open No. H3-164136) discloses a beverage comprising (a) at least 80 mass percent of water, (b) at least 0.05 mass percent of flavanols selected from the group consisting of catechin, catechin derivative, epicatechin, epicatechin derivative, and mixture thereof, (c) at least 0.2 mass percent of flavor substance selected from the group consisting of fruit flavor, plant flavor, and mixture thereof, and (d) 0.002 to 1.0 mass percent of caffeine (with the proviso that the ratio of caffeine versus flavanols is 1:1 to 1:30).

Patent Publication No. 3507433 (Japanese Patent Application Laid-Open No. 2001-197863) discloses a green tea extract, which is a green tea extract having 1% of soluble solid as a base, having (a) a mixture of catechins having a molecular weight range corresponding to an ultrafiltration membrane made from a polymer having a nominal cutoff molecular weight of 700 to 5000 daltons, the catechin mixture containing (1) at least 130 ppm of epicatechin, (2) at least 300 ppm of epigallocatechin, (3) at least 350 ppm of epigallocatechin gallate, and (4) at least 60 ppm of epicatechin gallate, (b) at least 50 ppm of theanine, (c) 10 ppm or less each of calcium, magnesium, manganese, aluminum, zinc, and iron ion, (d) an optical density of 0.06 or less when measured at 600 nm and further containing at least 450 ppm of caffeine.

Japanese Patent Application Laid-Open No. 2004-129669 discloses a containered tea beverage containing (a) 320 mg/500 mL to 1300 mg/500 mL of non-polymeric catechins and (b) caffeine, (c) the content ratio of non-epicatechins among non-polymeric catechins being 40 to 80 mass percent, (d) the mass ratio of non-polymeric catechins over caffeine being 5 to 8, (e) the mass ratio of non-polymeric catechins over total polyphenol being 0.88 to 1.0, and (f) turbidity being 0.7 or less, and containing high concentrations of non-polymeric catechins, with decreased bitter taste, harsh taste, and the like, and improved flavor.

Japanese Patent Application Laid-Open No. 2004-180535 discloses a method for removing caffeine selectively from a caffeine and catechin-containing component, in which a caffeine and catechin-containing component is dissolved in a solution of organic solvent and water mixed with a mass ratio of 9/1 to 1/9 and contacted with activated charcoal.

Japanese Patent Application Laid-Open No. 2004-35417 discloses an agent for increasing the total blood ketone concentration containing non-polymeric catechins (A) and caffeine (B) in which the content mass ratio [(A)/(B)] of non-polymeric catechins (A) over caffeine (B) is 0.3 or more.

Japanese Patent Application Laid-Open No. 2002-187848 discloses a *Camellia sinensis* polyphenol fraction containing 50% to 65% epigallocatechin-3-O-gallate, 13% to 20% epicatechin-3-O-gallate, 2% to 4% epicatechin, and 1.5% to 3% epigallocatechin, as well as 0.2% or less caffeine, obtained by a method for extracting a polyphenol fraction from *Camellia sinensis* (tea) containing 0.2 mass percent or less caffeine.

SUMMARY OF THE INVENTION

An object of the present invention is to provide a beverage that maintains a high concentration of catechin with high biological functionality, with improved flavor and product quality.

After earnest studies in view of the above problems, the present inventors observed that by adjusting to a predetermined range the concentration of catechins, the ratio of catechins in ester form to catechins in free form, and the ratio of catechins in ester form to caffeine, in a beverage, the original flavor of the beverage could be retained, but with decreased astringency, bitter taste and harsh taste, and furthermore, the occurrence of so-called sediment and cream down could be suppressed, and therefore the present inventors devised the present invention based on these observations.

That is to say, the present invention provides a beverage, which is a beverage containing catechins in ester form (A, mg/L), catechins in free form (B, mg/L), and caffeine (C, mg/L), the contents thereof being $$(A+B)=500 \text{ to } 6000 \text{ mg/L} \tag{1}$$

$$(A)/(A+B)=0.7 \text{ to } 1.0 \tag{2}$$

$$(A)/(C)=6 \text{ to } 27. \tag{3}$$

Catechins are major components constributing to the taste of tea beverages, among which catechin in free form is believed to contribute to the astringency of tea beverages.

In addition, catechins in ester form (EGCg, GCg, ECg, and Cg) compared to catechins in free form (EGC, GC, EC, C, (+) C) have stronger reactivity with other components, which is significant for health function.

Generally, the amount of catechin in ester form contained in a tea extract is on the order of 50% with respect to the total amount of catechin in ester form and catechin in free form.

The present invention is a beverage that allows, by increasing the catechin content while elevating the ratio of catechin in ester form within a predetermined range and adjusting the ratio between caffeine and catechin in ester form, the original flavor of the tea to be obtained with decreased astringency, bitter taste and harsh taste, and the catechin in ester form to be selectively and effectively ingested. In addition, the so-called sediment and cream down can be suppressed, which makes it an excellent beverage as a tea beverage.

DESCRIPTION OF THE PREFERRED EMBODIMENT

Hereinafter, an embodiment of a beverage of the present invention will be described. However, the scope of the present invention is not limited to the embodiment described below.

(Beverage)

This embodiment contains catechins in ester form (A, mg/L), catechins in free form (B, mg/L), and caffeine (C, mg/L), the contents thereof being $(A+B)$=500 to 6000 mg/L    (1)

$(A)/(A+B)$=0.7 to 1.0    (2)

$(A)/(C)$=6 to 27.    (3)

The amount of catechin in ester form (A) set in the present invention means the total amount of EGCg, GCg, ECg, and Cg, and the amount of catechin in free form (B) means the total amount of EGC, GC, EC, C, and (+) C. These amounts of catechin in ester form and amounts of catechin in free form are respectively determined by measuring with a method using high performance liquid chromatography detecting at ultraviolet wavelength. In addition, the amount of caffeine (C) can be simultaneously determined with the same measurement method as for catechin in ester form and catechin in free form.

(Requirement (1))

In the beverage of the embodiment, an amount of catechin in ester form (A) of not less than 350 mg/L is preferred, and not less than 500 mg/L is in particular preferred. In addition, an amount of 6000 mg/L or less is preferred, 3000 mg/L or less is more preferred, 2000 mg/L or less is in particular preferred, among which 1500 mg/L or less is especially more preferred.

In addition, in the beverage of the embodiment, a total amount of catechin in ester form (A) and catechin in free form (B) of not less than 500 mg/L is adequate, and a content of not less than 700 mg/L is more preferred. In addition, an amount of 6000 mg/L or less is adequate, 3000 mg/L or less is preferred, and 2800 mg/L or less is more preferred.

(Requirement (2))

In addition, a ratio of the amount of catechin in ester form (A) with respect to the total amount of catechin in ester form (A) and catechin in free form (B), that is (A)/[(A)+(B)], of not less than 0.7 is adequate, not less than 0.75 is preferred, and not less than 0.8 is more preferred. In addition, an amount of 1.0 or less is adequate.

If (A)+(B) is 500 to 6000 mg/L and (A)/[(A)+(B)] is 0.7 to 1.0 as indicated above, a beverage can be obtained which allows catechin with strong biological functionality to be ingested easily and inhibits excessive astringency.

(Requirement (3))

In addition, a ratio of the amount of catechin in ester form (A) with respect to the amount of caffeine (C), that is (A)/(C), of not less than 6 is adequate, and not less than 7 is preferred. In addition, a ratio of 27 or less is adequate, 26.6 or less is preferred, 20 or less is more preferred, among which 15 or less is in particular preferred. If (A)/(C) is 6 to 27, the bitter taste and harsh taste due to caffeine can be decreased; furthermore, the development of sediment and cream down can be suppressed, and the visual quality can also be positive.

(Preparation of Beverage)

In regard to the preparation of the beverage of the embodiments, (1) total amount and (2) mass ratio of catechin in ester form and catechin in free form, furthermore, (3) mass ratio of catechin in ester form and caffeine, may be adjusted by dissolving in water catechin in ester form (A), catechin in free form (B), and caffeine (C), so as to obtain a predetermined concentration, respectively; in particular, in the case of a tea beverage, extracting with water or hot water a non-fermented tea, a semi-fermented tea, a fermented tea, or a blend thereof, and then adding a tea extract to adjust the amount of catechin in ester form and catechin in free form allows natural tea flavor that can be drawn out, which is more preferred.

In addition, to prepare the beverage of the embodiment, extracting tea leaves of non-fermented tea, semi-fermented tea, or fermented tea with water or hot water at 40° C. to 100° C. and removing from the obtained extract 50 to 100 mass percent of catechin in ester form and catechin in free form, then adding the tea extract to adjust the ratio of the amount of catechin in ester form and the amount of catechin in free form is also preferred.

Hereinafter the preparation of the beverage will be explained in detail.

Tea leaves to be used as source include green teas, such as Sen-cha, Ban-cha, Gyokuro, Kamairi-cha, and Ten-cha as non-fermented tea; Oolong teas, such as Tie Guan Yin, Huang Jin Gui, and Shui Xian as semi-fermented tea; black teas, such as Darjeeling and Uva as fermented tea; or two or more kinds thereof blended. Water, warm water, or hot water, among which warm-hot water at 40° C. to 100° C. is preferred for the extraction of non-fermented tea, semi-fermented tea, fermented tea, or tea blend thereof, and in particular, hot water at 60° C. to 100° C. is more preferred.

(Removal of Catechin in Ester Form and Catechin in Free Form During Beverage Preparation)

Next, from the tea extract obtained as described above, a portion or the entirety, preferably 50% to 100%, more preferably 70% to 100%, of catechin in ester form and catechin in free form is removed temporarily to obtain an intermediate with a portion or the entirety of catechin in ester form and catechin in free form removed.

Examples of methods for removing catechin in ester form and catechin in free form that can be used include tea extract treatment processes, such as resin adsorption on a synthetic adsorption resin or the like, membrane separation by ultrafiltration membrane or reverse osmosis membrane, gel filtration chromatography method, and solvent extraction.

Among them, since resin adsorption using PVPP, which is a synthetic adsorption resin, can selectively adsorb catechin in ester form and catechin in free form, it is an excellent method for removing catechin in ester form and catechin in free form. In addition, the method for removing catechin in ester form and catechin in free form by adding PVPP in the course of extracting tea leaves of non-fermented tea, semi-fermented tea, or fermented tea in water or hot water, an invention by the present inventors (Japanese Patent No. 3315304), is particularly excellent. In so doing, the amount of synthetic adsorption resin PVPP can be selected suitably according to the amount or concentration of tea extract subjected to the treatment process.

(Adjustment of the Amount of Catechin During Beverage Preparation)

Next, the ratio of the amount of catechin in ester form and the amount of catechin in free form is adjusted by adding a tea extract to the intermediate in which a portion or the entirety of catechin in ester form and catechin in free form has been removed, as described above.

Herein, the tea extract may be a tea extract obtained by a method different from the method for the intermediate. For example, the tea extract is obtained by extracting tea leaves of non-fermented tea, semi-fermented tea, fermented tea with water, hot water, or water soluble organic solvent, further performing a predetermined purification and concentrating the product, a ratio of the amount of catechin in ester form with respect to the total amount of catechin in ester form and catechin in free form of not less than 0.7 being preferred, not less than 0.8 being more preferred. Adding this tea extract allows a beverage in which the amount of catechin in ester form with respect to the total amount of catechin in ester form and catechin in free form is 0.7 to 1.0.

In addition, commercialized tea extract concentrate can also be used; for instance, THEA-FLAN 30E, THEA-FLAN 30A, THEA-FLAN W, THEA-FLAN 90S (all manufactured by ITO EN), SUNFLAVONE HG (Taiyo Kagaku Co., Ltd.), POLYPHENON 70A, POLYPHENON E (Mitsui Norin Co., Ltd.), Theacalone 90S (Tokiwa Phytochemical Co., Ltd.), CTP-95 (Citimex), Greenselect (Indena), Tea-Fresh 80S (Japan Chlorophyll Co., Ltd.), TEAVIGO (DMS), or the like can be used.

In particular, THEA-FLAN 90S is excellent for elevating the amount of catechin in ester form with respect to the total amount of catechin in ester form and catechin in free form contained in the beverage of the embodiment since the amount of catechin in ester form with respect to the total amount of catechin in ester form and catechin in free form is 0.99.

Note that the ratio of the amount of catechin in ester form and the amount of catechin in free form can also be adjusted by adding one kind or more of each of the purified catechins, in particular, catechin in ester form EGCg, GCg, ECg, and Cg, when adding the tea extract or instead of adding the tea extract. In addition, water or hot water can be added to dilute.

As described above, by adding a tea extract with a predetermined composition to an intermediate obtained after extracting tea leaves of non-fermented tea, semi-fermented tea, or fermented tea with water or hot water and removing 50% or 100% of catechin in ester form and catechin in free form, the amount of catechin and the amount of caffeine, such as the total amount (Requirement 1) and mass ratio (Requirement 2) of catechin in ester form and catechin in free form, furthermore, the mass ratio of catechin in ester form and caffeine (Requirement 3), can be adjusted more easily and, in particular, the amount of catechin in ester form.

In addition, a beverage adjusted as described above is a beverage that allows catechin with a strong biological functionality, in particular, catechin in ester form, to be selectively and effectively ingested, and excessive astringency to be inhibited, while continuing to have a natural tea flavor.

(Other Formulations)

The beverage of the embodiment may have mixed in additives, such as oxidation inhibitor, emulsifying agent, preservative, pH adjuster, flavorant, seasoning, edulcorant, acidulant, and quality stabilizer, alone or in combination. For instance, vitamin C, vitamin E, cysteine, and the like can be used as oxidation inhibitor, and in particular, content of 0.005 to 0.05 mass percent in vitamin C is preferred. In addition, for instance, glucose, fructose, isomerized liquid sugar syrup, fructo-oligosaccharide, emulsified-oligosaccharide, soybean-oligosaccharide, cyclodextrin, Aspartame, *Momordica grosvenori* extract, and the like can be used as edulcorant, and in particular, a content of 0.05 to 1.5 mass percent in cyclodextrin is adequate. By mixing these additives alone or in combination, more excellent beverage can be provided. In addition, the concentration can be adjusted by suitably diluting with water, such that catechin, caffeine, and each component are at the drinking concentration.

(Intermediate and Utilization Thereof During Beverage Preparation)

Enough taste component (theanine, various amino acids, organic acids, and the like), aroma component (various esters, terpenes, alcohols, aldehydes, and the like), pigment (chlorophyll, carotenoids), and saccharide (various monosaccharides, oligosaccharides, polysaccharides, water soluble macromolecules, and the like) that the tea extract originally has remain in the intermediate obtained after extracting a portion or the entirety of catechin in ester form and catechin in free form from the tea extract, as described above. Consequently, the intermediate has flavor and taste the tea extract originally had and can be used as a taste composition with decreased astringency due to catechin.

In addition, the intermediate can be diluted by suitably using water or hot water. In addition, it can also be concentrated or solidified by removing solvent completely. As the concentration of various components, such as the taste component, of the diluted, concentrated, or solidified intermediate can be adjusted, it can be used preferably as an intermediate in the preparation of the beverage of the present invention; furthermore, it can also be used preferably as a taste composition.

EXAMPLE

In the following, examples according to the present invention will be shown; however, the scope of the invention is not limited to the examples.

(Measurement of Catechin in Ester Form, Catechin in Free Form, and Caffeine)

A high performance liquid chromatography apparatus manufactured by Waters Co. fitted with a column with an internal diameter of 4.6 mm and a length of 250 mm (J'sphere ODS-H80, YMC Co. Ltd.) was used to perform a gradient elution (flow rate 1.0 mL/min) with a mobile phase A solution: 5% acetonitrile (containing 0.1% phosphoric acid) and mobile phase B solution: 50% acetonitrile (containing 0.1% phosphoric acid) for separation at a column temperature of 40° C., and quantitation was performed using a pre-constructed calibration curve. A sample sampled from a beverage immediately after heat sterilization was carried out was subjected to a 0.45 μm filter, then, 10 μL of the filtrate thereof was injected to the high-performance liquid chromatography. The detection wavelength was set to UV 230 nm.

(Panelist Examination)

Four panelists were used to carry out an evaluation of the taste of the beverage. A portion of the beverage was placed in the mouth, and the degree of bitter taste and harsh taste was noted by the visual analog scale method (the higher the number, the stronger the degree). In addition, the occurrence of sediment and cream down and suitability as a tea beverage from the viewpoint of the balance of taste (suitable as tea beverage if suitability>5) were also evaluated similarly.

(Evaluation of Occurrence of Sediment and Cream Down)

Occurrence of sediment and cream down was evaluated visually.

Example 1

Green tea leaves made in Japan in the amount of 1.5 g were added to 60 mL of hot water (70° C.), extracted by stirring for 5 minutes to obtain a green tea extract; furthermore, 1 g of synthetic adsorption resin (PVPP) was introduced, stirred for 10 minutes, then the tea leaves and the synthetic adsorption resin were removed along with the adsorbed catechin in ester form and catechin in free form by filtration. To this extract, 0.5 g of cyclic oligosaccharide (manufactured by Nihon Shokuhin Kako Co., Ltd.), 0.345 g of tea extract (THEA-FLAN 90S: manufactured by Ito En Co., Ltd.; see Table 1 for composition), and a suitable amount of vitamin C were added, the pH was adjusted with sodium bicarbonate, then pure water was added to obtain a total volume of 250 mL. This solution was ultra-filtered; furthermore, heat sterilization (135° C., 30 seconds) was carried out to prepare Beverage 1. In addition, a 250 mL paper container was filled with this Beverage 1. The paper-containered beverage was conserved for one year at room temperature. Immediately before evaluation, the container was unsealed, and the beverage was transferred to a transparent bottle container.

TABLE 1

| EGC | EGCg | EC | ECg | GC | GCg | (+)C | Cg | Total catechin | Total polyphenol |
|---|---|---|---|---|---|---|---|---|---|
| n.d. | 43.14 | 0.82 | 16.30 | n.d. | 4.16 | n.d. | 1.40 | 65.82 | 99.20 |

Unit for the numbers in the table: %
n.d.: not detected

Example 2

Beverage 2 was prepared similarly to Example 1, except that 2.5 g of cyclic oligosaccharide (manufactured by Nihon Shokuhin Kako Co., Ltd.) was added. A 250 mL paper container was filled with this Beverage 2.

Example 3

Beverage 3 was prepared similarly to Example 1, except that the amount of the tea extract (THEA-FLAN 90S: manufactured by Ito En Co., Ltd.) was changed to 1.035 g. A 250 mL paper container was filled with this Beverage 3.

Regarding the beverages of Examples 1 to 3, concentration of catechin in ester form (A) (mg/L), concentration of catechin in free form (B) (mg/L), concentration of caffeine (C) (mg/L), panelist examination result and visual evaluation result after long-term conservation are shown for each beverage in Table 2.

No bitter taste and harsh taste was identified in all the Beverages 1 to 3, which, in addition, were excellent beverages as tea beverages. In addition, no occurrence of sediment and cream down due to long-term conservation could be identified visually.

Comparative Example 1

Green tea leaves (heavily-steamed tea, Chinese product) in the amount of 10 g was added to 1 L of warm water at 60° C. and extracted by stirring for 10 minutes. After the extraction, the tea leaves were removed, tea extract was cooled to below 25° C., and the entirety was filtered by nylon filtration cloth. Thereafter, a 190 g can container was filled with the filtrate, heat sterilized (120° C., 10 minutes) to prepare a beverage (Comparative-1). The can-containered beverage was conserved at room temperature for one year. Immediately before evaluation, the container was unsealed, and the beverage was transferred to a transparent bottle container.

Comparative Example 2

A beverage (Comparative-2) was prepared similarly to Comparative Example 1, except that instead of adding 10 g of green tea leaves (heavily-steamed tea, Chinese product), 10 g of green tea leaves (Kabuse-cha, Chinese product) was added.

Comparative Example 3

A beverage (Comparative-3) was prepared similarly to Comparative Example 1, except that instead of adding 10 g of green tea leaves (deep-steamed tea, Chinese product), 40 g of green tea leaves (Sen-cha, Japanese product) was added.

Comparative Example 4

The content of Beverage 3 conserved for one year at ordinary temperature was transferred to a transparent bottle container, commercial caffeine (manufactured by Wako Pure Chemical Industries, Ltd) was further added so that the caffeine concentration became 2000 mg/L to prepare a beverage (Comparative-4). The beverage was let to sit overnight at refrigeration temperature; the next day, after returning to room temperature, panelist examination and visual evaluation were carried out.

Regarding the beverages of Comparative Examples 1 to 4, concentration of catechin in ester form (A) (mg/L), concentration of catechin in free form (B) (mg/L), concentration of caffeine (C) (mg/L), panelist examination result and visual evaluation result are shown for each beverage in Table 2.

Bitter taste and harsh taste were strongly identified in Comparative-1 to Comparative-4, which were inappropriate beverages as tea beverages. In addition, due to the influence of long-term conservation or high caffeine ratio, notable occurrences of sediment and cream down were visually observed.

Note that, as cream down occurs more easily by cooling, in Comparative Example 4, a predetermined amount of caffeine was added to Beverage 3 after long-term conservation to prepare a beverage (Comparative-4), which was then conserved under refrigeration, and the next day, the beverage (Comparative-4) was returned to room temperature, and panelist examination and visual evaluation were carried out.

TABLE 2

| | Examples | | | Comparative Examples | | | |
|---|---|---|---|---|---|---|---|
| | Beverage 1 | Beverage 2 | Beverage 3 | Comparative 1 | Comparative 2 | Comparative 3 | Comparative 4 |
| epigallocatechin gallate (EGCg) mg/L | 298 | 272 | 972 | 155 | 110 | 332 | 972 |
| gallocatechin gallate (GCg) mg/L | 311 | 352 | 932 | 179 | 130 | 364 | 932 |
| epicatechin gallate (ECg) mg/L | 136 | 132 | 472 | 36 | 23 | 60 | 472 |
| catechin gallate (Cg) mg/L | 98 | 120 | 280 | 33 | 20 | 55 | 280 |
| epigallocatechin (EGC) mg/L | 3 | 0 | 0 | 50 | 43 | 273 | 0 |
| gallocatechin (GC) mg/L | 4 | 0 | 20 | 96 | 87 | 538 | 20 |
| epicatechin (EC) mg/L | 6 | 20 | 20 | 21 | 21 | 86 | 20 |
| catechin ((+) C) mg/L | 4 | 0 | 0 | 34 | 34 | 135 | 0 |
| catechin in ester form (A) mg/L | 843 | 876 | 2656 | 403 | 283 | 811 | 2656 |
| catechin in free form (B) mg/L | 17 | 20 | 40 | 201 | 185 | 1032 | 40 |
| caffeine (C) mg/L | 65.6 | 92 | 100 | 266 | 241 | 558 | 2000 |
| (A) + (B) | 860 | 896 | 2696 | 604 | 468 | 1843 | 2696 |
| (A)/[(A) + (B)] | 0.98 | 0.98 | 0.99 | 0.67 | 0.60 | 0.44 | 0.99 |
| (A)/(C) | 12.8 | 9.5 | 26.6 | 1.5 | 1.2 | 1.5 | 1.3 |
| Panelist evaluation (degree of bitter taste and harsh taste) | 1.6 | 1.7 | 2.8 | 6.8 | 5.6 | — | 10.0 |
| Panelist evaluation (adequacy as tea beverage) | 8.3 | 7.4 | 5.5 | 4.2 | 4.4 | — | 0.0 |
| Occurrence of sediment and cream down | not observed | not observed | not observed | notably observed | slightly observed | notably observed | notably observed |

What is claimed is:

1. A beverage;
    wherein said beverage comprises:
    (A) catechins in ester form (mg/L),
    (B) catechins in free form (mg/L), and
    (C) caffeine (mg/L);
    wherein the total concentration of catechins in the beverage is, (A)+(B)=500 to 6000 mg/L,
    the ratio of catechins in ester form to the total amount of catechins in the beverage is, (A)/[(A)+(B)]=0.7 to 1.0, and
    the ratio of catechins in ester form to caffeine is, (A)/(C) =6 to 27.

2. The beverage of claim 1, wherein occurrence of sediment and cream down is suppressed.

3. The beverage of claim 1, wherein the amount of catechins in ester form, (A), is from 350 mg/L to less than 6000 mg/L.

4. The beverage of claim 3, wherein the amount of catechins in ester form, (A), is from 500 mg/L to 3000 mg/L.

5. The beverage of claim 4 wherein the amount of catechins in ester form, (A), is from 500 mg/L to 2000 mg/L.

6. The beverage of claim 5, wherein the amount of catechins in ester form, (A), is from 500 mg/L to 1500 mg/L.

7. The beverage of claim 1, wherein the total concentration of catechins in the beverage, (A)+(B), is from 700 mg/L to 3000 mg/L.

8. The beverage of claim 7 wherein the total concentration of catechins in the beverage, (A)+(B), is from 700 to 2800 mg/L.

9. The beverage of claim 1, wherein the ratio of catechins in ester form to the total amount of catechins in the beverage, (A)/[(A)+(B)], is from 0.75 to 1.0.

10. he beverage of claim 9, wherein the ratio of catechins in ester form to the total amount of catechins in the beverage; (A)/[(A)+(B)], is from 0.8 to 1.0.

11. The beverage according to claim 1, wherein the ratio of catechins in ester form to caffeine, (A)/(C), is from 7 to 26.6.

12. The beverage according to claim 11 wherein the ratio of catechins in ester form to caffeine, (A)/(C), is from 7 to 20.

13. The beverage according to claim 12, wherein the ratio of catechins in ester form to caffeine, (A)/(C), is from 7 to 15.

* * * * *